United States Patent
Sawawatari

(10) Patent No.: US 7,782,048 B2
(45) Date of Patent: Aug. 24, 2010

(54) EDDY CURRENT TESTING METHOD, EDDY CURRENT TESTING DIFFERENTIAL COIL AND EDDY CURRENT TESTING PROBE FOR INTERNAL FINNED PIPE OR TUBE

(75) Inventor: Naoki Sawawatari, Osaka (JP)

(73) Assignee: Sumitomo Metal Industries, Ltd., Osaka (JP)

( * ) Notice: Subject to any disclaimer, the term of this patent is extended or adjusted under 35 U.S.C. 154(b) by 0 days.

(21) Appl. No.: 12/521,058

(22) PCT Filed: Dec. 4, 2007

(86) PCT No.: PCT/JP2007/073369

§ 371 (c)(1),
(2), (4) Date: Dec. 22, 2009

(87) PCT Pub. No.: WO2008/078513

PCT Pub. Date: Jul. 3, 2008

(65) Prior Publication Data

US 2010/0085044 A1 Apr. 8, 2010

(30) Foreign Application Priority Data

Dec. 26, 2006 (JP) ............................... 2006-350417

(51) Int. Cl.
*G01N 27/82* (2006.01)
(52) U.S. Cl. ....................................... 324/220; 324/240
(58) Field of Classification Search ......... 324/219–221, 324/228, 234, 237–243, 262
See application file for complete search history.

(56) References Cited

U.S. PATENT DOCUMENTS

2006/0017434 A1* 1/2006 Tenley et al. ................. 324/238
2006/0109001 A1* 5/2006 Suh et al. ..................... 324/232

FOREIGN PATENT DOCUMENTS

| JP | 58-166257 | 10/1983 |
| JP | 60-189850 | 12/1985 |
| JP | 3-285160 | 12/1991 |
| JP | 4-73863 | 6/1992 |
| JP | 4-290950 | 10/1992 |
| JP | 11-211704 | 8/1999 |
| JP | 2001-33393 | 2/2001 |
| JP | 2006-177941 | 7/2006 |

* cited by examiner

*Primary Examiner*—Bot L LeDynh
(74) *Attorney, Agent, or Firm*—Clark & Brody

(57) ABSTRACT

The invention provides an eddy current testing method for an internal finned pipe or tube which can securely detect a micro defect generated in a trough portion in an inner surface of the pipe or tube, even in the case that an inner surface shape of the internal finned pipe or tube is ununiform in a circumferential direction of the pipe or tube. The eddy current testing method in accordance with the invention detects a defect existing in a trough portion of the pipe or tube (P) by arranging a differential coil (2) constructed by a pair of coils (21, 22) having such a dimension as to be arranged within the trough portion of the pipe or tube (P) and coming away from each other in an axial direction (X) of the coil, within the trough portion of the pipe or tube (P) along a direction in which the trough portion of the pipe or tube (P) extends, and relatively moving the differential coil (2) in the direction in which the trough portion of the pipe or tube (P) extends.

8 Claims, 5 Drawing Sheets

EDDY CURRENT TESTING METHOD, EDDY CURRENT TESTING DIFFERENTIAL COIL AND EDDY CURRENT TESTING PROBE FOR INTERNAL FINNED PIPE OR TUBE

TECHNICAL FIELD

The present invention relates to an eddy current testing method, an eddy current testing differential coil and an eddy current testing probe for an internal finned pipe or tube. Particularly, the present invention relates to an eddy current testing method, an eddy current testing differential coil and an eddy current testing probe for an internal finned pipe or tube which can securely detect a micro defect (a crack-like micro defect) generated in a trough portion (or both the trough portion and a crest portion) of an inner surface of the pipe or tube, even in the case that an inner surface shape of the pipe or tube is ununiform in a circumferential direction of the pipe or tube. Hereinafter, "pipe or tube" is referred to as "tube" when deemed appropriate.

BACKGROUND ART

As a steel tube used in a manufacturing plant of an ethylene, there has been known a so-called internal finned tube forming a plurality of (normally eight to twelve) fins in which a cross sectional shape (a cross sectional shape perpendicular to an axial direction of a tube) has a triangular round thread ridge shape and extending in the axial direction of the tube (a shape which is in parallel to the axial direction of the tube or a sharp which is inclined to the axial direction of the tube) in an inner surface thereof, for the purpose of increasing a heat transfer efficiency.

FIG. 1 is a cross sectional view schematically showing an example of the internal finned tube mentioned above. As shown in FIG. 1, an internal finned tube P is formed in its inner surface by crest portions (fins) M and trough portion R which are alternately provided in a circumferential direction of the tube. The internal finned tube P as mentioned above is normally manufactured in accordance with a centrifugal casting method and a hot extrusion tube manufacturing method which is typified by Ugine Sejournet process, by using a Fe base alloy having high Cr and high Ni as a raw material.

However, in the case of manufacturing the internal finned tube P by the hot extrusion tube manufacturing method, since the Fe base alloy having high Cr and high Ni serving as the raw material is inferior in a hot working performance, there is a characteristic that a shape of the crest portion M, particularly a shape of its top portion is hard to come to a predetermined shape. Accordingly, a countermeasure, for example, enlarging an extrusion ratio or the like is applied for making the shape of the crest portion M in the predetermined shape, however, in this case, there is a case that a micro crack-like defect K extending in an axial direction of a tube is generated in the trough portion R (particularly at the appropriately center of a trough bottom portion Rs), and a defect such as a fold flaw, a crack or the like is generated in the crest portion M.

Further, in the case of manufacturing the internal finned tube P in accordance with a cold rolling by a mandrel having a fin which is aligned with the shape of the fin formed in the inner surface by using a cylindrical raw tube, there is a case that a defect such as a crack, a sticking or the like in the cold rolling is generated in the crest portion M or the trough portion R.

If the generation of the defect as mentioned above is missed out on, it comes to a factor causing a severe accident during use of the tube P. Accordingly, it is necessary to take a measure for inspecting before shipping a product so as to fix up and remove the defect, and a non-destructive inspecting method having a high efficiency is desired.

Conventionally, there have been proposed an ultrasonic testing method, a fluorescent penetrant testing method, an eddy current testing method and the like as the non-destructive inspecting method detecting the defect generated in the inner surface of the internal finned tube.

As the ultrasonic testing method, for example, in Japanese Unexamined Patent Publication No. 10-274643, there has been proposed a method of making a shape echo from a side surface of the crest portion M forming an obstacle to identification of a defect echo from a defect K extremely small, as shown in FIG. 5. Specifically, there has been proposed a method of inputting an ultrasonic beam from an outer surface side of the tube at an angle of incidence θ (θ=90 to 70 degrees) in such a manner that the ultrasonic beam is approximately orthogonal to a diameter line L of the tube passing through the center of the trough bottom portion Rs, with respect to the center of the trough bottom portion Rs in the inner surface of the internal finned tube P.

The method described in the publication mentioned above generates no problem in the case that the inner surface shape of the internal finned tube P is approximately uniform in a circumferential direction of the tube, specifically in the case that a thickness t (see FIG. 1) of the trough bottom portion Rs is approximately even. However, if the inner surface shape is ununiform in the circumferential direction of the tube, that is, the thickness t of the trough bottom portion Rs is uneven, it becomes hard to identify the shape echo from the side face of the crest portion M and the defect echo from the defect K, and there is a disadvantage that it is not possible to detect the defect K at all, in the case that the unevenness of the thickness t is significant.

Further, in Japanese Unexamined Patent Publication No. 11-211704, there has been proposed a technique inputting an ultrasonic beam from a outer surface of a tube at an angle (90 to 70 degrees) in such a manner that the ultrasonic beam is approximately orthogonal to a diameter line of a tube passing through the center of the trough bottom portion with respect to the center of the trough bottom portion of the inner surface of the internal finned tube and detecting a defect by using an image processing. Specifically, there has been proposed a technique displaying by B scope after binarizing a testing signal detected by inputting the ultrasonic beam so as to separate into plural levels of signals, and detecting the defect generated in the trough bottom portion by image processing the B scope display image.

In accordance with the technique described in the publication mentioned above, it is possible to identify the defect echo and the shape echo on the image, in the case that a depth of the defect is large. However, in the case that the depth of the defect is small, it is hard to identify both the echoes and there is a risk of wrongly determining the defect. Further, since the imaging and the image processing are necessary, there is a disadvantage that it is hard to apply to a high speed inspection, and a cost of the processing apparatus becomes high.

Further, as the fluorescent penetrant testing method, for example, there has been proposed the following method, in Japanese Unexamined Patent Publication No. 2001-33393. In other words, first, a nozzle is inserted to an inner surface of an internal finned tube, a fluorescent penetrant fluid is sprayed from the nozzle, and the fluorescent penetrant fluid is applied to an inner surface of a whole length of the internal finned tube. Next, after a predetermined penetrating time of the fluorescent penetrant fluid has passed, the other nozzle is inserted to the inner surface of the internal finned tube, and water or a cleaning fluid is sprayed from this nozzle. Accordingly, the fluorescent penetrant fluid penetrating to the flaw is left in an inner portion of the flaw, and an extra fluorescent penetrant fluid attached to the inner surface is removed. Next, after drying the inner surface of the internal finned tube from which the extra fluorescent penetrant fluid is removed, an ultraviolet light including a visible light is radiated to the inner surface of the internal finned tube while inserting an inspection head. Further, the radiated inner surface of the tube is photographed by a camera head provided in the inspection head, and a determination is made whether the defect is present by an image reflected on a monitor.

Since the method described in the publication mentioned above requires the work taking a lot of trouble such as the applying work, the removing work and the drying work of the fluorescent penetrant fluid, there is a disadvantage that the method is not suitable for the inspection in which a high efficiency is demanded.

Further, since the eddy current testing method can efficiently detect the defect existing in the detected surface, the eddy current testing method is widely used as the non-destructive inspecting method of the inner surface of the tube. However, in the general eddy current testing method using a so-called internal inserted coil, since a distance between the internal inserted coil and the trough bottom portion of the internal finned tube becomes long, it is hard to detect a micro defect existing in the trough bottom portion.

Accordingly, for example, in Japanese Unexamined Patent Publication No. 58-166257, there has been proposed an eddy current testing method using a so-called external reference type coil, the method scanning an eddy current testing probe structured such that a detecting coil is embedded in a leading end portion and a reference coil is embedded at a position which is at a suitable length away from the detecting coil, along a spiral groove (corresponding to the trough portion of the internal finned tube).

However, in the eddy current testing method using the external reference type coil as described in the publication mentioned above, a noise tends to be generated due to a liftoff fluctuation of the detecting coil, ununiformity of the inner surface shape of the tube and the like, and there is a risk that the S/N ratio is lowered and the defect is missed out.

Further, in Japanese Unexamined Patent Publication No. 4-290950, there has been proposed an inner surface detecting head of an inner helically finned tube. The inner surface detecting head carries out eddy current testing by using a guide doubling as an eddy current testing sensor around which a coil for the eddy current testing is wound around a pair of fins respectively engaging with the trough portions of the tube and opposing to each other at the same time of being provided for a visual observation by imaging a tube inner circumferential surface reflected to a pyramidal mirror provided so as to be rotatable around a tube axis by a TV camera. Further, in the publication mentioned above, there is described that the defect existing in the trough bottom portion of the tube is detected by the eddy current testing sensor.

However, since a surface area of the coil is large in the coil as described in the publication mentioned above, that is, the coil wound around the spiral trough portion of the tube, the coil is not suitable for detecting the micro defect.

DISCLOSURE OF THE INVENTION

The present invention is made to solve the problem of conventional techniques described above, and an object of the present invention is to provide an eddy current testing method, an eddy current testing differential coil and an eddy current testing probe for an internal finned pipe or tube which can securely detect a micro defect generated in a trough portion (or both the trough portion and a crest portion) in a inner surface of a pipe or tube, even in the case that an inner surface shape of the internal finned pipe or tube is ununiform in a circumferential direction of the pipe or tube.

In order to achieve the object, the present invention provides an eddy current testing method of an internal finned pipe or tube in which crest portions and trough portions alternately provided in a circumferential direction of the pipe or tube in an inner surface of the pipe or tube and extending in an axial direction of the pipe or tube are formed, wherein a defect existing in the trough portion of the pipe or tube is detected by arranging a differential coil constructed by a pair of coils having such a dimension as to be arranged within the trough portion of the pipe and coming away from each other in an axial direction of the coil, within the trough portion of the pipe or tube along a direction in which the trough portion of the pipe or tube extends, and relatively moving the differential coil in the direction in which the trough portion of the pipe or tube extends.

In accordance with the invention mentioned above, the differential coil constructed by a pair of coils which come away from each other in the axial direction of the coil is arranged within the trough portion of the pipe or tube along the direction in which the trough portion of the pipe or tube extends, and is relatively moved in the direction in which the trough portion of the pipe or tube extends (the differential coil is moved while fixing the pipe or tube, or the pipe or tube is moved while fixing the differential coil). Accordingly, the distance between each of the coils and the trough bottom portion of the pipe or tube becomes shorter in comparison with the case that the general internal inserted coil is used, and it is possible to precisely detect the defect. Further, in the case of making the axial direction of a pair of coils in parallel to the direction in which the pipe or tube extends, the direction of the eddy current generated by each of the coils becomes orthogonal to the direction in which the trough portion of the pipe or tube extends. Accordingly, it is possible to precisely detect the defect generated in the trough portion (particularly in the approximately center of the trough bottom portion) and extending in the axial direction of the pipe or tube (more specifically, the direction in which the trough portion extends). Further, in the present invention, the self comparison type coil (the coil outputting the difference of the detection signal in each of the coils) is used. Accordingly, since it is possible to reduce the noise due to the liftoff fluctuation caused by the relative movement of the coil and ununiformity of the inner surface shape of the pipe or tube (it is easy to discriminate the frequency between the defect signal and the noise signal) in comparison with the case that the external reference type coil is used, and the S/N ratio becomes large, it is possible to detect the micro defect.

Here, in the present invention, "the internal finned pipe or tube in which the crest portion and the trough portion extending in the axial direction of the pipe or tube are formed" means to include not only the internal finned pipe or tube in which the crest portion and the trough portion extending in parallel to the axial direction of the pipe or tube are formed, but also the internal finned pipe or tube in which the spiral crest portion and trough portion extending while being tilted with respect to the axial direction of the pipe or tube are formed. Further, the number of the fins is normally between eight and twelve, however, is not limited thereto.

Preferably, the coil is structured such that a wire portion facing the trough bottom portion of the trough portion is wound in a curved shape in a cross sectional view which is orthogonal to the axial direction of the coil, in such a manner that a gap between the coil and the testing region of the trough portion becomes approximately constant in a state of being arranged within the trough portion of the pipe or tube.

In accordance with the preferred structure mentioned above, the wire portion facing the trough bottom portion of the coil is wound like the curve in the cross sectional view which is orthogonal to the axial direction of the coil, in such a manner that the gap between the coil and the testing region of the trough portion becomes approximately constant in the state in which the coil is arranged within the trough portion of the pipe or tube. Accordingly, it is possible to keep the liftoff of the coil approximately constant with respect to any region within the testing region, and it is possible to inhibit the noise from being generated due to the difference of the liftoff. Further, it is possible to keep the detection sensitivity of the coil approximately constant with respect to any region within the testing region.

Here, in the present invention, "the testing region of the trough portion" means a position coming to a subject to be detected the defect in the inner surface of the pipe or tube forming the trough portion. For example, the trough bottom portion and the vicinity position thereof are set to the testing region. Further, "the gap between the coil and the testing region of the trough portion" means a shortest distance between the wire forming the coil and the testing region of the trough portion. It is possible to appropriately decide what curve the wire portion facing the trough bottom portion is wound, in correspondence to the cross sectional shape of the testing region of the trough portion of the tested pipe or tube (the cross sectional shape which is orthogonal to the direction in which the trough portion extends).

Preferably, the coil is structured such that the wire portion facing the trough bottom portion of the trough portion is wound in a circular arc shape, and a wire portion facing an axis of the pipe or tube is wound in a linear shape, in a cross sectional view which is orthogonal to the axial direction of the coil, in such a manner that a gap between the coil and the testing region of the trough portion becomes approximately constant in a state of being arranged within the trough portion of the pipe or tube.

It is often the case that the cross sectional shape of the trough bottom portion and the vicinity position of the internal finned pipe or tube (the cross sectional shape which is orthogonal to the direction in which the trough portion extends) is designed as a circular arc shape. Accordingly, in the case that the trough bottom portion and the vicinity position thereof are set to the testing region, it is possible to make the gap between the coil and the testing region of the trough portion approximately constant by winding the wire portion facing the trough bottom portion of the coil in the circular arc shape, such as the preferred structure mentioned above. On the other hand, there is a nature if a rate of an area (an area of the face opposing to the coil) of the defect with respect to the surface area of the whole of the coil is large, the defect signal detected by the coil becomes large. Therefore, since it is possible to reduce the surface area of the coil in comparison with the case that the whole of the wire is wound in the circular arc shape, by linearly winding the wire portion facing the axis of the pipe or tube (that is, the opposite portion to the portion facing the trough bottom portion) which does not affect directly to the testing, such as the preferred structure, and it is possible to enlarge the defect signal, it is possible to enhance the S/N ratio accordingly.

In order to achieve the object, the present invention provides a differential coil used in eddy current testing of an internal finned pipe or tube in which crest portions and trough portions alternately provided in a circumferential direction of the pipe or tube in an inner surface of the pipe or tube and extending in an axial direction of the pipe or tube are formed, wherein the differential coil constructed by a pair of coils having such a dimension as to be arranged within the trough portion of the pipe or tube and coming away from each other in an axial direction of the coil, and wherein the coil is structured such that a wire portion facing the trough bottom portion of the trough portion is wound in a curved shape in a cross sectional view which is orthogonal to the axial direction of the coil, in such a manner that a gap between the coil and the testing region of the trough portion becomes approximately constant in a state of being arranged within the trough portion of the pipe or tube along a direction in which the trough portion of the pipe or tube extends.

Preferably, the coil is structured such that the wire portion facing the trough bottom portion of the trough portion is wound in a circular arc shape, and a wire portion facing an axis of the pipe or tube is wound in a linear shape, in a cross sectional view which is orthogonal to the axial direction of the coil, in such a manner that a gap between the coil and the testing region of the trough portion becomes approximately constant in a state of being arranged within the trough portion of the pipe or tube.

In order to achieve the object, the present invention provides an eddy current testing method of an internal finned pipe or tube in which crest portions and trough portions alternately provided in a circumferential direction of the pipe or tube in an inner surface of the pipe or tube and extending in an axial direction of the pipe or tube are formed. The method comprises the steps of: arranging a first differential coil constructed by a pair of coils having such a dimension as to be arranged within the trough portion of the pipe or tube and coming away from each other in an axial direction of the coil, within the trough portion of the pipe or tube along a direction in which the trough portion of the pipe or tube extends; arranging a second differential coil constructed by a pair of coils having such a dimension as to be arranged in an inner side in a diametrical direction of the pipe or tube than a top portion of the crest portion of the pipe or tube and coming away from each other in an axial direction of the coil, in the inner side in the diametrical direction of the pipe or tube than the top portion of the crest portion of the pipe or tube in such a manner as to become approximately in parallel to the axial direction of the pipe or tube; and detecting a defect existing in the trough portion of the pipe or tube by the first differential coil and detecting a defect existing in the crest portion of the pipe or tube by the second differential coil, by integrally moving the first differential coil and the second differential coil relatively in the direction in which the trough portion of the pipe or tube extends.

In accordance with the invention mentioned above, it is possible to precisely detect the defect generated in the trough portion (particularly in the approximately center of the trough bottom portion) by the first differential coil (corresponding to the differential coil mentioned above). Further, the second differential coil constituted by a pair of coils which come away from each other in the axial direction of the coil is arranged in the inner side in the diameter direction of the pipe or tube than the top portion of the crest portion of the pipe or tube in such a manner as to be approximately in parallel to the axial direction of the pipe or tube, and is moved relatively in the direction in which the trough portion of the pipe or tube extends (corresponding to the direction in which the crest portion extends) (the second differential coil is moved while fixing the pipe or tube, or the pipe or tube is moved while fixing the second differential coil). Accordingly, it is possible to precisely detect the defect generated in the crest portion (particularly the approximately center of the top portion). In the case of making the axial direction of a pair of coils of the second differential coil in parallel to the axial direction of the pipe or tube, the direction of the eddy current generated by each of the coils becomes orthogonal to the direction in which the crest portion of the pipe or tube extends. Accordingly, it is possible to precisely detect the defect generated in the crest portion (particularly in the approximately center of the top portion) and extending in the axial direction of the pipe or tube (more specifically the direction in which the crest portion extends). Further, since the differential coil is used, the noise due to the liftoff fluctuation caused by the relative movement of the coil and ununiformity of the inner surface shape of the pipe or tube are reduced (the frequency discrimination can be easily carried out between the defect signal and the noise signal) in comparison with the case that the external reference type coil of an absolute method is used, and the S/N ratio becomes large. Accordingly, it is possible to detect the micro defect. Further, in accordance with the present invention, since the first differential coil and the second differential coil are integrally moved relatively in the direction in which the trough portion of the pipe or tube extends (the direction in which the crest portion of the pipe or tube extends), it is possible to simultaneously detect the defect generated in both the trough portion and the crest portion.

Further, in order to achieve the object, the present invention provides a probe used in eddy current testing of an internal finned pipe or tube in which crest portions and trough portions alternately provided in a circumferential direction of the pipe or tube in an inner surface of the pipe or tube and extending in a axial direction of a pipe or tube are formed, the probe comprising: a cylindrical core body having such a dimension as to be arranged in an inner side in a diametrical direction of the pipe or tube than a top portion of the crest portion of the pipe or tube; a first differential coil attached to an outer circumferential surface of the core body; and an elastic body interposed between the core body and the first differential coil, and energizing the first differential coil outward in a diametrical direction of the core body, wherein the first differential coil constructed by a pair of coils having such a dimension as to be arranged within the trough portion of the pipe or tube, and coming away from each other in an axial direction of the coil, and wherein the coil is attached to the core body in such a manner as to be arranged within the trough portion of the pipe or tube in a state of being along a direction in which the trough portion of the pipe or tube extends, at a time when the core body is inserted to the pipe or tube, and is structured such that a wire portion facing the trough bottom portion of the trough portion is wound in a curved shape in a cross sectional view which is orthogonal to the axial direction of the coil, in such a manner that a gap between the coil and the testing region of the trough portion becomes approximately constant in a state of being arranged within the trough portion of the pipe or tube.

In accordance with the invention mentioned above, in the case of the internal finned pipe or tube in which the crest portion and the trough portion extending in parallel to the axial direction of the pipe or tube are formed, it is possible to relatively move the first differential coil energized by the elastic body in the direction in which the trough portion of the pipe or tube extends within the trough portion of the pipe or tube, in the state in which the gap between the first differential coil and the testing region becomes approximately constant by relatively moving the core body in the axial direction of the pipe or tube. Further, in the case of the internal finned pipe or tube in which the spiral crest portion and trough portion extending while tilting with respect to the axial direction of the pipe or tube are formed, it is possible to relatively move the first differential coil energized by the elastic body in the direction in which the trough portion of the pipe or tube extends within the trough portion of the pipe or tube, in the state in which the gap between the first differential coil and the testing region becomes approximately constant by relatively moving the core body in the axial direction of the pipe or tube and relatively rotating the core body in the circumferential direction of the pipe or tube. Accordingly, it is possible to precisely detect the defect generated in the trough portion and extending in the axial direction of the pipe or tube (the direction in which the trough portion extends).

Preferably, the probe further comprises a second differential coil constructed by a pair of coils having such a dimension as to be arranged in an inner side in the diametrical direction of the pipe or tube than a top portion of the crest portion of the pipe or tube, having a wire portion wound along an outer circumferential surface of the core body, and coming away from each other in an axial direction of the core body.

In accordance with the preferred structure mentioned above, it is possible to detect the defect generated in the crest portion by the second differential coil at the same time of detecting the defect generated in the trough portion by the first differential coil, by relatively moving (or relatively rotating in the circumferential direction of the pipe or tube in addition thereto) the core body in the axial direction of the pipe or tube.

In accordance with the invention mentioned, it is possible to securely detect a micro defect generated in a trough portion (or both the trough portion and a crest portion) of an inner surface of the pipe or tube, even in the case that an inner surface shape of the pipe or tube is ununiform in a circumferential direction of the pipe or tube.

BRIEF DESCRIPTION OF THE DRAWINGS

FIG. 2 (FIG. 2A and FIG. 2B) are views schematically showing an example of a structure of an eddy current testing probe which is inserted into a tube for executing an eddy current testing method of an internal finned tube in accordance with the present invention, in which

BEST MODE FOR CARRYING OUT THE INVENTION

A description will be given below of an embodiment in accordance with the present invention appropriately with reference to the accompanying drawings.

Figure 2A:
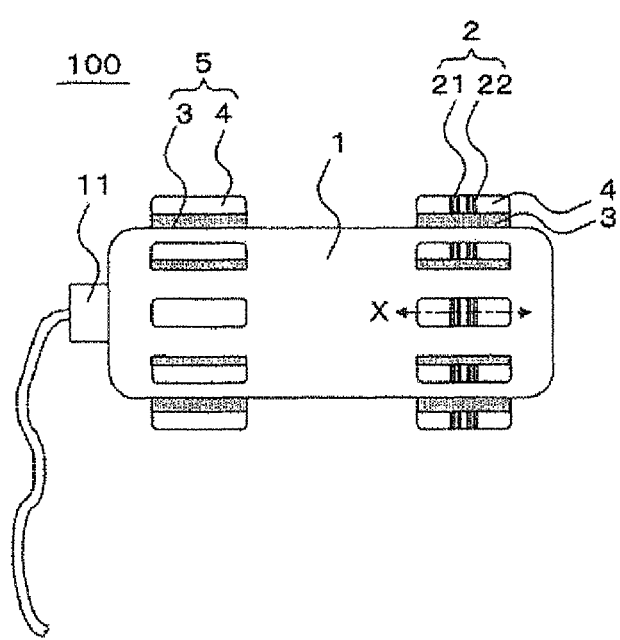
FIG. 2A shows a front elevational view.
Figure 2B:
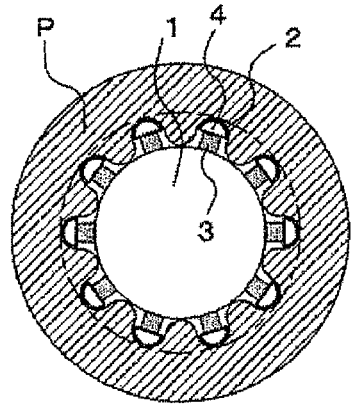
FIG. 2B shows a side elevational view expressing a state of being inserted into the tube.

FIG. 2 (FIG. 2A and FIG. 2B) are views schematically showing an example of a structure of an eddy current testing probe which is inserted into a tube for executing an eddy current testing method for an internal finned tube in accordance with the present invention, in which FIG. 2A shows a front elevational view, and FIG. 2B shows a side elevational view expressing a state of being inserted into the tube. As shown in FIG. 2A and FIG. 2B, an eddy current testing probe (hereinafter, refer appropriately to as the "probe") 100 in accordance with the present embodiment is provided with a cylindrical core body 1 having such a dimension that can be arranged in an inner side in a diameter direction of the tube P than a top portion of a crest portion of the tube P, a first differential coil 2 attached to an outer circumferential surface of the core body 1, and an elastic body 3 interposed between the core body 1 and the first differential coil 2, and energizing the first differential coil 2 outward in a diametrical direction of the core body 1. The eddy current testing probe 100 in accordance with the present embodiment is provided with ten first differential coils 2 and ten elastic bodies 3 which are attached at even gaps in a circumferential direction of the core body 1 in such a manner as to test flaw in all trough portions of the tube P in which ten fins (crest portions) being in parallel to a axial direction of the tube P are formed at a stroke.

The structure is made such that an alternating current is input to the core body 1 from an external portion (an alternating current power supply or the like) via a connector 11, and the alternating current is fed to the first differential coil 2. Further, a detected signal of the first differential coil 2 is output to an external portion (a flaw detector or the like) via the connector 11, and testing is carried out based on the detected signal. In this case, it is preferable that at least an outer surface of the core body 1 is formed by an insulating material such as a resin, in such a manner as to have a little influence on an electromagnetic field generated by the first differential coil 2.

Figure 1:
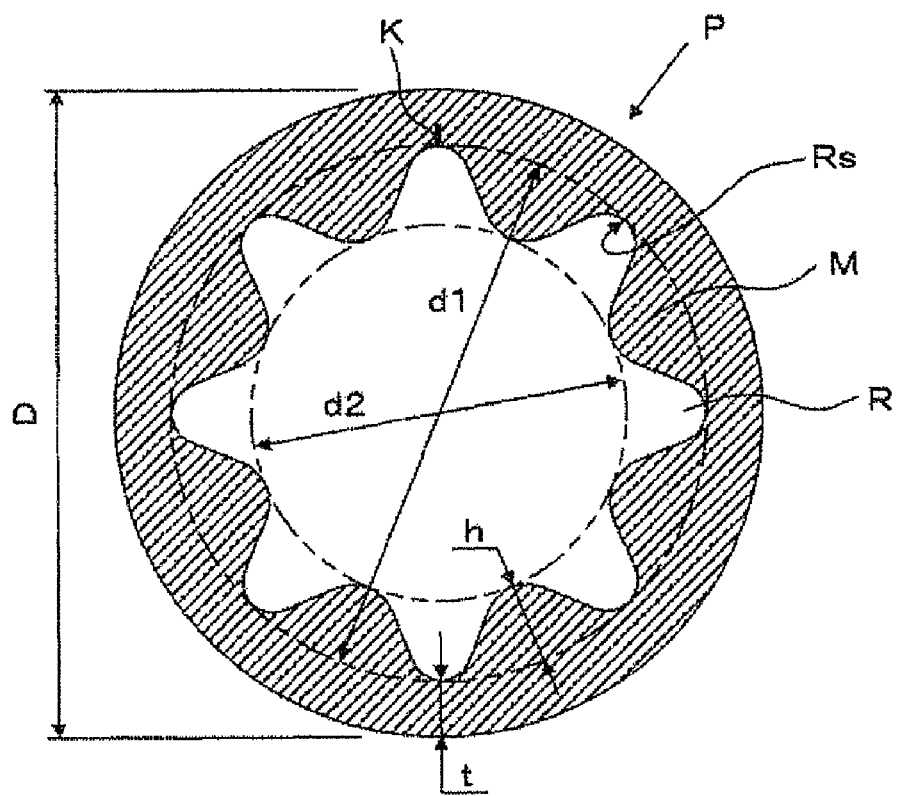
FIG. 1 is a cross sectional view schematically showing an example of the internal finned tube.

The first differential coil 2 is constructed by a pair of coils 21 and 22 which have such a dimension as to be arranged within the trough portion of the tube P, have approximately coinciding axes and come away from each other in an axial direction (a direction shown by an arrow X in FIG. 2A). The first differential coil 2 (the coils 21 and 22) in accordance with the present embodiment is structured such that a wire portion facing a trough bottom portion of the trough portion is wound in a curved shape in a cross sectional view which is orthogonal to the axial direction X, in such a manner that a gap between the first differential coil 2 and a testing region (the trough bottom portion and its vicinity region, in the present embodiment) of the trough portion becomes approximately constant, in a state of being arranged within the trough portion of the tube P (a state shown in FIG. 2B). Specifically, since the cross sectional shape of the trough bottom portion and the vicinity position of the tube P is designed in a circular arc shape in the present embodiment, the first differential coil 2 is structured such that the wire portion facing the trough bottom portion of the trough portion is wound in the circular arc shape (a semicircular arc shape in the present embodiment), and the wire portion facing the axis of the tube P is wound in a linear shape. Further, in specific, the wire of the first differential coil 2 is wound in a semicircular arc shape having a height (a dimension in a diametrical direction of the core body 1) which is equal to or less than a half of a height h (see FIG. 1) of the crest portion of the tube P.

Each of the coils 21 and 22 is wound around a core material 4 formed by an insulating material such as a resin, a non-magnetic metal material or the like. The core material 4 is fixed to the elastic body 3 in its lower face, and is energized outward in the diametrical direction of the core body 1 by the elastic body 3. Accordingly, the first differential coil 2 (the coils 21 and 22) wound around the core material 4 is energized outward in the diametrical direction of the core body 1. In this case, since the trough portion of the tube P in the present embodiment extends in parallel to the axial direction of the tube P, the first differential coil 2 is attached to the coil body 1 in such a manner that an axial direction thereof becomes approximately in parallel to the axial direction of the core body 1 (the axial direction of the core body 1 becomes approximately in parallel to the axial direction of the tube P at a time when the probe 100 is inserted to the tube P). Accordingly, the first differential coil 2 is arranged within the trough portion of the tube P in a state in which the axial direction thereof becomes approximately in parallel to the direction in which the trough portion of the tube P extends at a time of inserting the probe 100 into the tube P. It is possible to relatively move in the direction in which the trough portion extends.

In the present embodiment, an outer surface of at least the coils 21 and 22 is covered with an insulating material (for example, an insulating tape or the like may be used) for protecting the coils 21 and 22. Since the coils 21 and 22 are energized outward in the diametrical direction of the core body 1 by the elastic body 3, the insulating material covering each of the coils 21 and 22 is always pressed against the testing region of the trough portion of the tube P at a time of inserting the probe 100 into the tube P. Accordingly, even if the probe 100 is relatively moved in the axial direction of the tube P at a time of detecting the flaw, it is possible to keep the gap between each of the coils 21 and 22 and the testing region of the trough portion of the tube P approximately constant.

Alternatively, it is possible to employ such a structure that the other position of the core material 4 than the position at which the coils 21 and 22 are wound protrudes outward in the diametrical direction of the core body 1 than the outer surfaces of the coils 21 and 22 (the outer surface of the insulating material in the case of covering the outer surfaces of the coils 21 and 22 by the insulating material). In this case, the protruding portion of the core material 4 is always pressed against the testing region of the trough portion of the tube P at a time of inserting the probe 100 into the tube P. In accordance with the structure mentioned above, it is possible to keep the gap between each of the coils 21 and 22 and the testing region of the trough portion of the tube P approximately constant, at a time of relatively moving the probe 100 in the axial direction of the tube P at the testing time.

Figure 3:
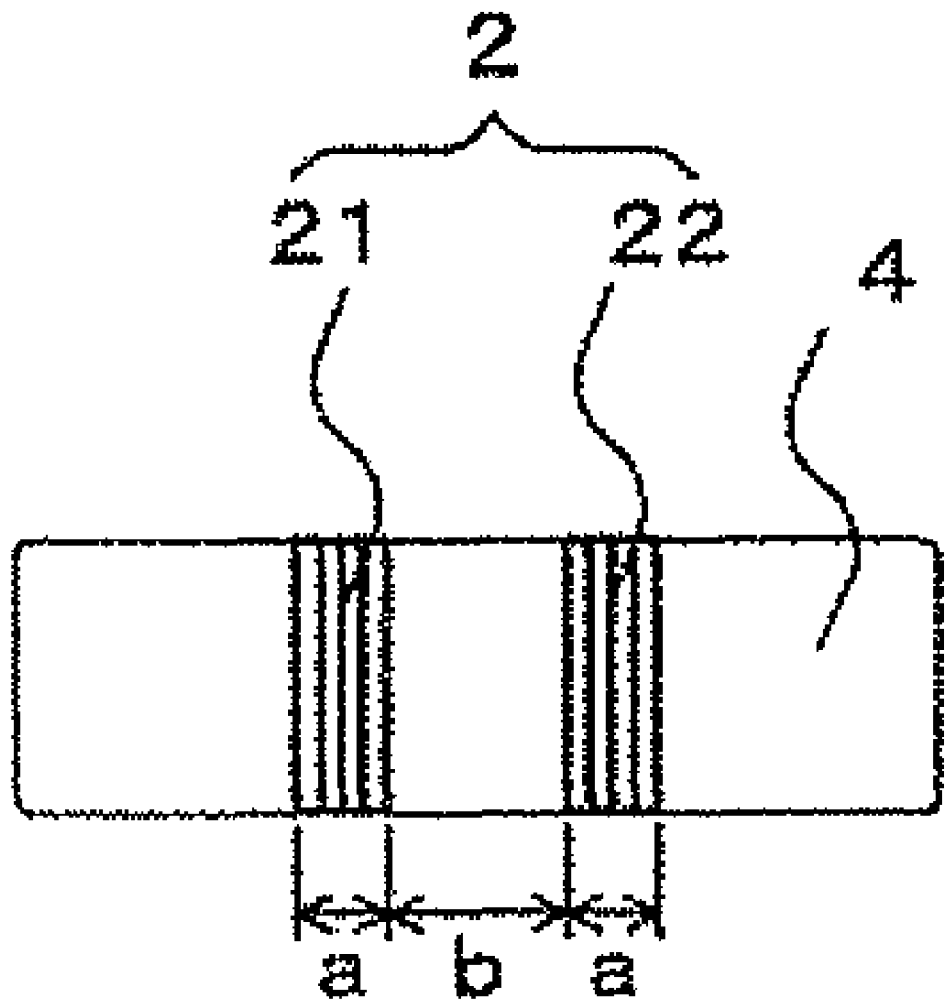
FIG. 3 is a front elevational view showing a differential coil shown in FIG. 2A and FIG. 2B in an enlarged manner.

In this case, it is preferable to set the gap between each of the coils 21 and 22 and the testing region of the trough portion of the tube P equal to or less than 2 mm. Further, it is preferable to set the difference of the gap between the regions within the testing region in the same cross section (the cross section which is orthogonal to the direction in which the trough portion extends) equal to or less than 1 mm. Specifically, the cross sectional shape (the cross sectional shape which is orthogonal to the axial direction of the coils 21 and 22) of the coils 21 and 22 and the thickness of the insulating material (or the height of the protruding portion of the core material 4) may be decided in such a manner that the set values can be obtained. Further, the smaller a wire width (a dimension denoted by reference symbol a in FIG. 3) and a wire gap (a dimension denoted by reference symbol b in FIG. 3) of each of the coils 21 and 22, the higher frequency region a frequency of a defect signal detected by the first differential coil 2 is shifted. Accordingly, it is advantageous in a point that it is easy to discriminate a frequency between the defect signal and a noise signal having more low frequency region components than the defect signal (an S/N ratio is improved by applying a high pass filter to the detection signal of the differential coil 2). Further, the smaller the wire width a of each of the coils 21 and 22 is, the larger a ratio (defect area of the surface facing the coil)/(surface area of the coil) is with respect to the same defect. Accordingly, in case that the wire width a is small, the detection signal of each of the coils 21 and 22 becomes larger with respect to the small defect, and a defect detection performance is improved. In this case, if the wire width a of each of the coils 21 and 22 is too small, there is a case that the detection signal of each of the coils 21 and 22 is saturated with respect to the defect having a length which goes beyond the wire width a, and the large defect is undervalued. Further, if the coil wire gap b is too small, the detection signal of the differential coil 2 becomes small at a time of testing by relatively moving the probe 100, and there is generated a disadvantage that the defect is undervalued. Accordingly, the wire width a and the wire gap b of each of the coils 21 and 22 may be appropriately decided in correspondence to the magnitude, the kind and the like of the defect to be detected.

As the elastic body 3, it is possible to preferably employ a spring formed by a nonmagnetic metal material or the like, a rubber or the like. A height of the elastic body 3 (a dimension in the diametrical direction of the core body 1) may be appropriately decided in such a manner that the insulating material covering each of the coils 21 and 22 (or the protruding portion of the core material 4) comes to a state of being always pressed against the testing region of the trough portion of the tube P (i.e., a state in which the elastic body 3 shrinks), at a time of inserting the probe 100 into the tube P.

In this case, the eddy current testing probe 100 in accordance with the present embodiment is provided with ten guide members 5 which are attached to the outer circumferential surface of the core body 1. The respective guide members 5 are attached to positions which come away from the attached positions of the respective first differential coils 2 in the axial direction of the core body 1, and each of them is provided with the same kind of core material as the core material 4 around which the first differential coil 2 is wound, and the same kind of elastic body as the elastic body 3 supporting the core material 4. Since the core material of the guide member 5 is pressed against the trough portion of the tube P at a time of inserting the probe 100 into the tube P, based on the provision of the guide member 5 in the probe 100, it is possible to stabilize a degree of parallelization between the axial direction of the core body 1 and the axial direction of the tube P.

Further, the same kind of differential coil as the differential coil 2 may be provided in place of the guide member 5. In this case, since the testing region of the trough portion of the tube is detected in an overlapping manner, it is possible to further prevent a miss of the defect.

The first differential coil 2 is relatively moved together with the core body 1 in the direction (the axial direction of the tube P) in which the trough portion of the tube P extends, by inserting the core body 1 of the eddy current testing probe 100 having the structure described above into the tube P (by relatively moving the core body 1 in the axial direction of the tube P), whereby it is possible to detect the defect existing in the trough portion.

In this case, in the present embodiment, the description is given of the structure in which the probe 100 is provided with ten first differential coils 2 in such a manner that it is possible to detect the flaw of all the (ten) trough portions of the tube P at a stroke, however, the present invention is not necessarily limited thereto, but may employ a structure in which a part of the first differential coils 2 is replaced by the guide member 5. In other words, the probe may be structured such as to be provided with a less number of first differential coils 2 than the number of the trough portions of the tube P. For example, in the case of detecting the flaw in all the trough portions by employing a structure provided with one first differential coil 2 (remaining nine elements are the guide members 5), the testing may be repeated by finishing the testing with regard to one trough portion, thereafter taking out the probe from the tube P, and relatively rotating the core body 1 in the circumferential direction of the tube P in such a manner that the first differential coil 2 is relatively movable along the non-detected trough portion.

Further, in the present embodiment, since there is exemplified the case that the tube P in which the trough portion extends in parallel to the axial direction of the tube P is made of the test object, the description is given of the structure in which the first differential coil 2 is attached to the core body 1 in such a manner that the axial direction of the first differential coil 2 becomes approximately in parallel to the axial direction of the core body 1. However, in the case that the internal finned tube in which the spiral crest portion and trough portion extending while tilting with respect to the axial direction of the tube are formed is made of the test object, it is possible to attach in a state in which the axial direction of the first differential coil 2 is tilted to the axial direction of the core body 1 depending on an inclination angle of the trough portion. In this case, it is possible to test the flaw in the same manner as the tube P in which the trough portion extends in parallel to the axial direction of the tube, by relatively moving the core body 1 in the axial direction of tube and relatively rotating the core body 1 in the circumferential direction of the tube. In other words, it is possible to relatively move the first differential coil 2 in the direction in which the trough portion of the tube extends within the trough portion of the tube, in a state in which the gap between the first differential coil 2 and the testing region becomes approximately constant.

Figure 4:
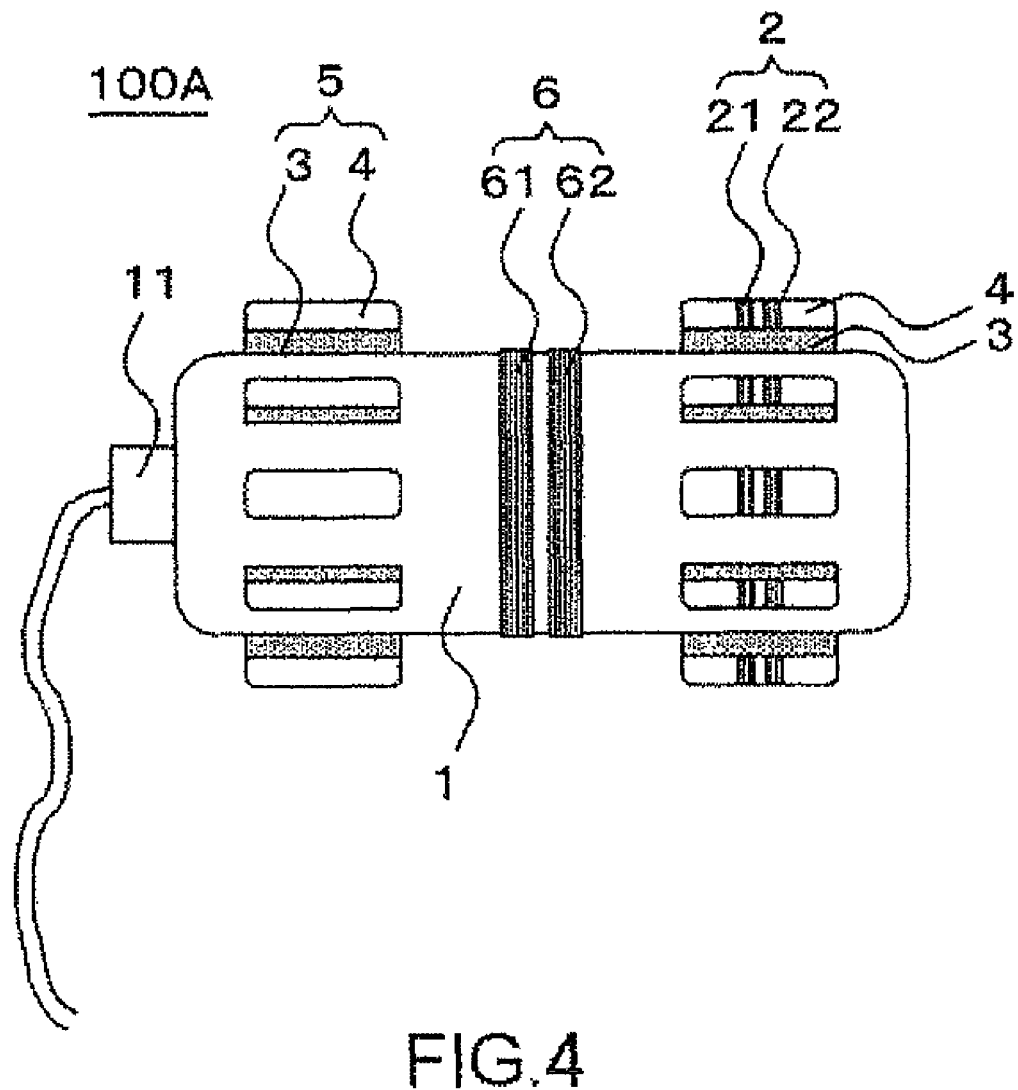
FIG. 4 is a front elevational view schematically showing the other example of the structure of the eddy current testing probe of the present invention.
Figure 5:
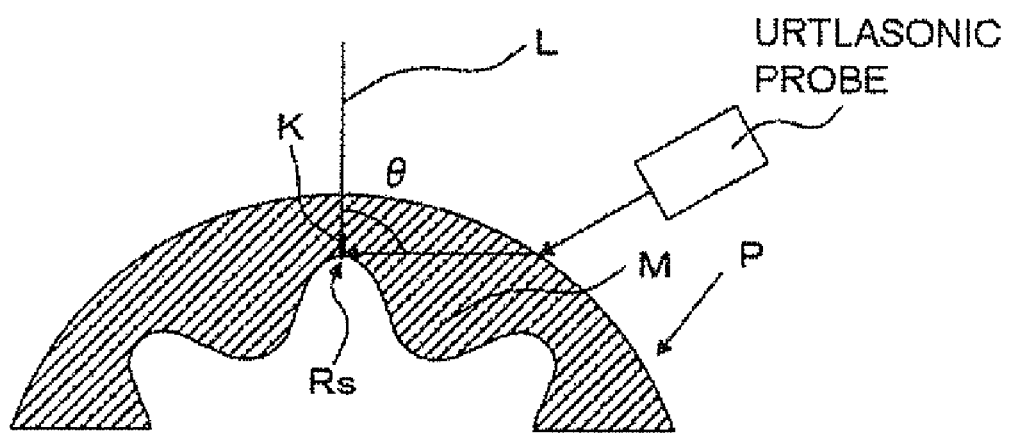
FIG. 5 is a schematic cross sectional view explaining a conventional ultrasonic testing method for an internal finned tube.

Further, in the present embodiment, the description is given of the structure of the eddy current testing probe 100 for detecting the defect existing in the trough portion, however, in the case of also detecting the defect existing in the crest portion, an eddy current testing probe 100A as shown in FIG. 4 may be used.

FIG. 4 is a front elevational view schematically showing the other example of the structure of the eddy current testing probe. As shown in FIG. 4, the probe 100A in accordance with the present structure example is structured such as to be provided with a second differential coil 6 which is constructed by a pair of coils 61 and 62 coming away from each other in the axial direction of the core body 1, in addition to the structure provided in the probe 100 shown in FIG. 2A and FIG. 2B mentioned above. The coils 61 and 62 have such a dimension as to be arranged in an inner side in a diametrical direction of the tube than a top portion of the crest portion of the tube, and have a wire wound along the outer circumferential surface of the core body 1.

In accordance with the probe 100A, it is possible to detect the defect generated in the crest portion by the second differential coil 6 at the same time of detecting the defect generated in the trough portion by the first differential coil 2, by relatively moving the core body 1 in the axial direction of the tube (or relatively rotating it in the circumferential direction of the tube in addition thereto).

In this case, if the gap between the coils 61 and 62 and the top portion of the crest portion of the tube is too large, a detecting sensitivity of the coil is lowered. Accordingly, it is preferable to set the dimension of the coils 61 and 62 (the dimension in the diametrical direction of the core body 1) somewhat smaller than a crest portion corresponding diameter d2 (see FIG. 1) of the tube P.

Further, in the case of simultaneously applying the alternating current to the first differential coil 2 and the second differential coil 6, it is preferable to use testing frequencies (frequencies of the alternating currents applied to the coils 2 and 6) which are different from each other, since electromagnetic fields generated by the respective differential coils 2 and 6 are prevented from interfering with each other.

Example

The feature of the present invention will be further clarified by showing an example.

An artificial flaw is formed in a trough bottom portion of an internal finned tube (material: Fe—Cr—Ni alloy, outer diameter D: 56.6 mm, trough portion thickness t: 6.35 mm, crest portion height h: 6.35 mm, see FIG. 1) in which ten fins are formed in parallel to a axial direction of a tube, and a testing test in accordance with the eddy current testing method of the present invention is carried out.

Specifically, as the artificial flaw, there are provided four kinds of (totally eight kinds of) notches respectively having depths 0.3 mm, 0.5 mm, 0.8 mm, and 1.0 mm with regard to each of two kinds of widths (dimension in a direction which is orthogonal to the axial direction of the tube) 0.5 mm and 1.0 mm while having a length (dimension in the axial direction of the tube) 25 mm. Further, there are provided two kinds of through drill holes respectively having diameters 1.6 mm and 2.2 mm. These ten kinds of artificial flaws are lined up in a direction in which the trough bottom portion extends, and are detected sequentially by moving the eddy current testing probe 100 shown in FIG. 2A and FIG. 2B in the axial direction of the tube. The present example employs only the detection signal of one first differential coil 2 corresponding to the trough bottom portion provided with the artificial flaw among ten first differential coils 2 shown in FIG. 2A and FIG. 2B. With regard to the shape of the first differential coil 2, it is employed a semicircular arch shape in which a wire portion facing the trough bottom portion of the tube is wound in a semicircular arc shape in such a manner as to come to a similar shape to a testing region (the trough bottom portion and its vicinity region) of the tube, and a wire portion facing the axis of the tube is wound in a linear shape. Further, a gap between the first differential coil 2 and the testing region of the trough portion of the tube P is kept at a fixed value about 0.5 mm, by setting a thickness of the insulating material covering the first differential coil 2 to about 0.5 mm.

Further, a test is carried out by setting wire widths, wire gaps and testing frequencies of the coils 21 and 22 constructing the first differential coil 2 to two conditions shown in the following Table 1.

TABLE 1

| Wire width and Wire gap of differential coil (wire width:wire gap:wire width) | Testing frequency |
| --- | --- |
| 5 mm:2 mm:5 mm | 32 kHz |
| 1 mm:1 mm:1 mm | 256 kHz |

Results of the testing test described above will be shown in Table 2. In this case, "differential coil (1:1:1)" shown in Table 2 means the differential coil 2 in which the wire width, the wire gap and the wire width of the coils 21 and 22 equal to 1 mm, 1 mm and 1 mm, and "differential coil (5:2:5)" means the differential coil 2 in which the wire width, the wire gap and the wire width of the coils 21 and 22 equal to 5 mm, 2 mm and 5 mm. Further, the results of the testing test are evaluated by a ratio (S/N ratio) between a magnitude of the signal (S) of the artificial flaw detected by the differential coil 2 and a magnitude of the noise signal (N).

TABLE 2

| Shape of artificial flaw | | | S/N ratio | |
| --- | --- | --- | --- | --- |
| Kind of flaw | Width (mm) | Depth (mm) | Differential coil (1:1:1) Testing frequency: 256 kHz | Differential coil (5:2:5) Testing frequency: 32 kHz |
| Notch (length 25 mm) | 0.5 | 0.3 | 2.5 | 2 |
| | | 0.5 | 5.3 | 4 |
| | | 0.8 | 8.7 | 7 |
| | | 1 | 12.7 | 10.5 |
| | 1 | 0.3 | 4.7 | 3 |
| | | 0.5 | 7 | 5 |
| | | 0.8 | 12 | 7 |
| | | 1 | 14.3 | 8 |
| Through drill hole | 1.6 mm diameter | | 11.7 | 11.6 |
| | 2.2 mm diameter | | 14.7 | 18.5 |

As shown in Table 2, in the case that the artificial flaw is the through drill hole, a sufficient S/N ratio can be obtained. On the other hand, in the case that the artificial flaw is the notch, the S/N ratio is lowered in accordance that the flaw becomes smaller, and there is a case that the S/N ratio <5.0 is satisfied. However, if the wire width and wire gap of the coils 21 and 22 are set smaller (the wire width=1 mm, and the wire gap=1 mm, in the present example), the S/N ratio becomes comparatively high, and the S/N ratio ≧5.0 can be obtained even in the micro notch having the width 0.5 mm and the depth 0.5 mm. If the S/N ratio ≧5.0 can be obtained with respect to such the micro flaw as mentioned above, there is no problem practically, and a defect can be detected with high precision by the eddy current testing method in accordance with the present invention.

What is claimed is:

1. An eddy current testing method of an internal finned pipe or tube in which crest portions and trough portions alternately provided in a circumferential direction of the pipe or tube in an inner surface of the pipe or tube and extending in an axial direction of the pipe or tube are formed,
    wherein a defect existing in the trough portion of the pipe or tube is detected by arranging a differential coil constructed by a pair of coils having such a dimension as to be arranged within the trough portion of the pipe or tube and coming away from each other in an axial direction of the coil, within the trough portion of the pipe or tube along a direction in which the trough portion of the pipe or tube extends, and relatively moving the differential coil in the direction in which the trough portion of the pipe or tube extends.

2. The eddy current testing method of an internal finned pipe or tube as claimed in claim 1, wherein the coil is structured such that a wire portion facing the trough bottom portion of the trough portion is wound in a curved shape in a cross sectional view which is orthogonal to the axial direction of the coil, in such a manner that a gap between the coil and the testing region of the trough portion becomes approximately constant in a state of being arranged within the trough portion of the pipe or tube.

3. The eddy current testing method of an internal finned pipe or tube as claimed in claim 2, wherein the coil is structured such that the wire portion facing the trough bottom portion of the trough portion is wound in a circular arc shape, and a wire portion facing an axis of the pipe or tube is wound in a linear shape, in a cross sectional view which is orthogonal to the axial direction of the coil, in such a manner that a gap between the coil and the testing region of the trough portion becomes approximately constant in a state of being arranged within the trough portion of the pipe or tube.

4. A differential coil used in eddy current testing of an internal finned pipe or tube in which crest portions and trough portions alternately provided in a circumferential direction of the pipe or tube in an inner surface of the pipe or tube and extending in an axial direction of the pipe or tube are formed,
   wherein the differential coil constructed by a pair of coils having such a dimension as to be arranged within the trough portion of the pipe or tube and coming away from each other in an axial direction of the coil, and
   wherein the coil is structured such that a wire portion facing the trough bottom portion of the trough portion is wound in a curved shape in a cross sectional view which is orthogonal to the axial direction of the coil, in such a manner that a gap between the coil and the testing region of the trough portion becomes approximately constant in a state of being arranged within the trough portion of the pipe or tube along a direction in which the trough portion of the pipe or tube extends.

5. The differential coil used in eddy current testing of an internal finned pipe or tube as claimed in claim 4, wherein the coil is structured such that the wire portion facing the trough bottom portion of the trough portion is wound in a circular arc shape, and a wire portion facing an axis of the pipe or tube is wound in a linear shape, in a cross sectional view which is orthogonal to the axial direction of the coil, in such a manner that a gap between the coil and the testing region of the trough portion becomes approximately constant in a state of being arranged within the trough portion of the pipe or tube.

6. An eddy current testing method of an internal finned pipe or tube in which crest portions and trough portions alternately provided in a circumferential direction of the pipe or tube in an inner surface of the pipe or tube and extending in an axial direction of the pipe or tube are formed, the method comprising the steps of;
   arranging a first differential coil constructed by a pair of coils having such a dimension as to be arranged within the trough portion of the pipe or tube and coming away from each other in an axial direction of the coil, within the trough portion of the pipe or tube along a direction in which the trough portion of the pipe or tube extends;
   arranging a second differential coil constructed by a pair of coils having such a dimension as to be arranged in an inner side in a diametrical direction of the pipe or tube than a top portion of the crest portion of the pipe or tube and coming away from each other in an axial direction of the coil, in the inner side in the diametrical direction of the pipe or tube than the top portion of the crest portion of the pipe or tube in such a manner as to become approximately in parallel to the axial direction of the pipe or tube; and
   detecting a defect existing in the trough portion of the pipe or tube by the first differential coil and detecting a defect existing in the crest portion of the pipe or tube by the second differential coil, by integrally moving the first differential coil and the second differential coil relatively in the direction in which the trough portion of the pipe or tube extends.

7. A probe used in eddy current testing of an internal finned pipe or tube in which crest portions and trough portions alternately provided in a circumferential direction of the pipe or tube in an inner surface of the pipe or tube and extending in a axial direction of a pipe or tube are formed, the probe comprising:
   a cylindrical core body having such a dimension as to be arranged in an inner side in a diametrical direction of the pipe or tube than a top portion of the crest portion of the pipe or tube;
   a first differential coil attached to an outer circumferential surface of the core body; and
   an elastic body interposed between the core body and the first differential coil, and energizing the first differential coil outward in a diametrical direction of the core body,
   wherein the first differential coil constructed by a pair of coils having such a dimension as to be arranged within the trough portion of the pipe or tube, and coming away from each other in an axial direction of the coil, and
   wherein the coil is attached to the core body in such a manner as to be arranged within the trough portion of the pipe or tube in a state of being along a direction in which the trough portion of the pipe or tube extends, at a time when the core body is inserted to the pipe or tube, and is structured such that a wire portion facing the trough bottom portion of the trough portion is wound in a curved shape in a cross sectional view which is orthogonal to the axial direction of the coil, in such a manner that a gap between the coil and the testing region of the trough portion becomes approximately constant in a state of being arranged within the trough portion of the pipe or tube.

8. The probe used in eddy current testing of an internal finned pipe or tube as claimed in claim 7, further comprising a second differential coil constructed by a pair of coils having such a dimension as to be arranged in an inner side in the diametrical direction of the pipe or tube than a top portion of the crest portion of the pipe or tube, having a wire portion wound along an outer circumferential surface of the core body, and coming away from each other in an axial direction of the core body.

* * * * *